US009956635B2

(12) United States Patent
Kobayashi et al.

(10) Patent No.: US 9,956,635 B2
(45) Date of Patent: *May 1, 2018

(54) METHOD FOR ESTIMATING CARBOXYLIC ACID GAS CONCENTRATION AND SOLDERING APPARATUS

(71) Applicant: ORIGIN ELECTRIC COMPANY, LIMITED, Saitama (JP)

(72) Inventors: Hideo Kobayashi, Saitama (JP); Naoto Ozawa, Saitama (JP); Jun Matsuda, Saitama (JP)

(73) Assignee: Origin Electric Company, Limited, Saitama (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/358,653

(22) Filed: Nov. 22, 2016

(65) Prior Publication Data

US 2017/0072493 A1    Mar. 16, 2017

Related U.S. Application Data

(63) Continuation of application No. 15/112,400, filed as application No. PCT/JP2015/050100 on Jan. 6, 2015, now Pat. No. 9,513,211.

(30) Foreign Application Priority Data

Jan. 22, 2014 (JP) .................................. 2014-009261

(51) Int. Cl.
*G01N 21/3504* (2014.01)
*G01N 33/00* (2006.01)
(Continued)

(52) U.S. Cl.
CPC .................. *B23K 3/08* (2013.01); *B23K 1/20* (2013.01); *G01J 5/0014* (2013.01);
(Continued)

(58) Field of Classification Search
CPC .. G01N 21/3504; G01N 33/0047; B23K 1/20; B23K 3/08; G01J 5/0014
See application file for complete search history.

(56) References Cited

U.S. PATENT DOCUMENTS

| | | | | |
|---|---|---|---|---|
| 2010/0320148 | A1* | 12/2010 | Yukumoto | ........... B01D 61/362 210/641 |
| 2010/0320258 | A1* | 12/2010 | Sawada | ................ B23K 1/0016 228/180.22 |
| 2013/0105558 | A1* | 5/2013 | Abe | ..................... B23K 1/0016 228/179.1 |

* cited by examiner

*Primary Examiner* — David Porta
*Assistant Examiner* — Mindy Vu
(74) *Attorney, Agent, or Firm* — Squire Patton Boggs (US) LLP

(57) ABSTRACT

To provide a method for estimating a concentration of carboxylic acid gas, which is capable of measuring safely the concentration of carboxylic acid gas such as formic acid gas or the like in a chamber of a soldering apparatus in real time, and a soldering apparatus capable of estimating the concentration of the carboxylic acid gas in the chamber. The method includes the steps of measuring a surface temperature of a same object placed in the chamber at a same point in time by using a thermometer (first thermometer) for measuring a temperature without any influence of infrared absorption by carboxylic acid, and a radiation thermometer (second thermometer) for measuring a temperature by infrared in a wavelength region that the carboxylic acid absorbs, and estimating the concentration of the carboxylic acid gas in the chamber on the basis of a temperature difference ($\Delta Tx$) between temperatures indicated by the first and second thermometers. The soldering apparatus includes a heating stage (30), a gas introducing part (25) for introducing a mixed gas of an inert gas and a carboxylic acid gas, a gas discharging part (26), first thermometer (37) and second thermometer (38).

7 Claims, 6 Drawing Sheets

(51) Int. Cl.
*G01J 5/00* (2006.01)
*B23K 1/20* (2006.01)
*B23K 3/08* (2006.01)
*G01N 25/00* (2006.01)

(52) U.S. Cl.
CPC ......... *G01N 21/3504* (2013.01); *G01N 25/00* (2013.01); *G01N 33/0047* (2013.01)

METHOD FOR ESTIMATING CARBOXYLIC ACID GAS CONCENTRATION AND SOLDERING APPARATUS

CROSS-REFERENCE TO RELATED APPLICATION

This application is a continuation of U.S. application Ser. No. 15/112,400, filed Jul. 18, 2016, which is a national phase entry of International Application No. PCT/JP2015/050100, filed Jan. 6, 2015, which claims priority to Japan Application No. 2014-009261, filed Jan. 22, 2014.

TECHNICAL FIELD

The present invention relates to a method for estimating a carboxylic acid gas concentration in a chamber and relates to a soldering apparatus capable of estimating the carboxylic acid gas concentration in the chamber, suitably used in a soldering process or the like for a semiconductor. More particularly, the present invention relates to a method for estimating the carboxylic acid gas concentration by utilizing an infrared absorption of a specific wavelength by carboxylic acid and also relates to a soldering apparatus applicable to the method.

BACKGROUND ART

When a solder bump is formed on a semiconductor chip, a solder is deposited on a pad and then a shape of the solder bump is changed from a mushroom shape to a hemisphere shape, followed by reflowing to join by soldering. According to a conventional soldering method, in order to form a uniform solder bump, a surface oxide film of a solder is removed with a flux to cleanse the surface of the solder bump.

However, according to a soldering process that uses a flux, small cavities (voids) may be formed in the solder bump due to decomposition of the flux. These cavities not only deteriorate electrical and mechanical properties of a formed solder joint but also destroy flatness of a semiconductor with the solder bump and may generate a harmful effect on the following semiconductor joining process. A volatile material of the decomposed flux may contaminate the inside of a reflow processor and as a result a maintenance cost may increase. In addition, a flux residue remains frequently on a semiconductor substrate to cause metal corrosion, and degradation of performance of an assembly. Further, according to a method in which the flux residue is cleansed and removed after reflow step, a time required for soldering increases because of addition of after-cleansing as a new processing step.

Therefore, as a soldering method without use of a flux, there is known a method of reducing with formic acid the solder and the joined members such as a substrate and electrode (see Patent Documents 1 to 3 and others). According to such a method of reduction, when a temperature of joined members on which the solder is mounted reaches a predetermined temperature, the solder is exposed to a reducing gas including formic acid to perform an acid treatment in which a surface oxide film is removed and are then molten to be processed.

An acid treatment by formic acid is usually performed with vaporized gaseous formic acid because a reduction start temperature of formic acid is about 150° C., and a boiling temperature of formic acid is about 100° C. At that time, to know a concentration of formic acid gas in a chamber, a method of collecting a gas in the chamber and analyzing the collected gas by gas chromatograph or a FTIR (Fourier Transform Infrared Spectrometer) may be used. However, in these cases, there are problems, for example, further provision of analyzers such as the gas chromatograph, FTIR or the like, and requirement of safety measures for collecting highly irritating formic acid in a high temperature gas state. Further, there is also a problem that the formic acid concentration cannot be measured in real time because an analysis takes time.

Further, the formic acid gas after the end of the acid treatment is forcibly discharged out of the chamber. At that time, a method of collecting the gas in the chamber and analyzing the collected gas by the gas chromatograph, the FTIR or the like to confirm whether the formic gas in the chamber is sufficiently discharged faces the same problem.

Therefore, in the acid treatment with a carboxylic acid gas such as formic acid or the like, a method of conveniently and safely measuring the carboxylic acid gas concentration in the chamber in real time is desired.

PRIOR ART DOCUMENTS

Patent Documents

Patent Document 1: JP 2001-244618 A
Patent Document 2: JP 2007-125578 A

SUMMARY OF THE INVENTION

Problem to be Solved by the Invention

In view of the above-described problems, an object of the present invention is to provide a method for estimating a concentration of carboxylic acid gas, which is capable of measuring safely the concentration of carboxylic acid gas such as formic acid gas or the like in a chamber of a soldering apparatus in real time, and a soldering apparatus capable of estimating the concentration of the carboxylic acid gas in the chamber.

Means for Solving the Problem

The present invention provides the following method and apparatus to solve the above-described problems.
(1) A method for estimating a concentration of a carboxylic acid gas in a chamber, the carboxylic acid gas introduced into the chamber being for reaction, the method including: measuring a surface temperature of a same object placed in the chamber at a same point in time by using a thermometer (first thermometer) for measuring a temperature without any influence of infrared absorption by carboxylic acid, and a radiation thermometer (second thermometer) for measuring a temperature by infrared in a wavelength region that the carboxylic acid absorbs; and estimating the concentration of the carboxylic acid gas in the chamber on the basis of a temperature difference ($\Delta Tx$) between temperatures indicated by the first thermometer and the second thermometer.
(2) A method for estimating a concentration of a carboxylic acid gas in a chamber, the carboxylic acid gas introduced into the chamber being for reaction, the method including: measuring, while changing a concentration of the carboxylic acid gas for reaction, a surface temperature of a same object placed in the chamber at a same point in time by using a thermometer (first thermometer) for measuring a temperature without any influence of infrared absorption by carboxylic acid, and a radiation thermometer (second thermometer)

for measuring a temperature by infrared in a wavelength region that the carboxylic acid absorbs; preparing in advance a calibration line showing a relationship of the carboxylic acid gas concentration and a temperature difference (ΔT) by obtaining the temperature difference (ΔT) between temperatures indicated by the first thermometer and the second thermometer; and estimating the concentration of the carboxylic acid gas in the chamber on the basis of the prepared calibration line and the temperature difference (ΔTx) between temperatures indicated by the first thermometer and the second thermometer for a surface temperature of the same object placed in the chamber.

(3) The method for estimating a concentration of a carboxylic acid gas according to above (2), further including: preparing the calibration lines showing a relationship of the carboxylic acid gas concentration and the temperature difference (ΔT) under a plurality of conditions different in an acid treatment temperature; obtaining a relational expression showing a relationship of a gradient of the calibration line and the acid treatment temperature, obtaining a gradient of the calibration line in a predetermined acid treatment temperature from the relational expression, and estimating the concentration of carboxylic acid gas in the chamber on the basis of the gradient of the calibration line and the temperature difference (ΔTx).

(4) The method for estimating a concentration of a carboxylic acid gas according to any one of above (1) to (3), wherein the first thermometer is a radiation thermometer for measuring a temperature by the infrared in a wavelength region that the carboxylic acid does not absorb.

(5) The method for estimating a concentration of a carboxylic acid gas according to any one of above (1) to (3), wherein the method is applied to an object having a surface temperature between normal temperature and 350° C.

(6) The method for estimating a concentration of a carboxylic acid gas according to above (4), wherein the method is applied to an object having a surface temperature between normal temperature and 350° C.

(7) A method for estimating an amount of carboxylic acid, the method including: estimating a concentration of a carboxylic acid gas in a chamber by using the method of estimating a concentration of a carboxylic acid gas according to any one of above (1) to (6); and calculating an amount of carboxylic acid in the chamber from an estimated value of the concentration of the carboxylic acid, a capacity of the chamber and an internal pressure of the chamber.

(8) A soldering apparatus capable of estimating a concentration of a carboxylic acid gas in a chamber, the soldering apparatus including: a heating stage; a gas introducing part for introducing a mixed gas of an inert gas and a carboxylic acid gas; and a chamber having a gas discharging part; wherein the chamber comprises a thermometer (first thermometer) for measuring a temperature without any influence of infrared absorption by carboxylic acid, and a radiation thermometer (second thermometer) for measuring a temperature by infrared in a wavelength region that the carboxylic acid absorbs.

(9) The soldering apparatus according to above (8), wherein the first thermometer is a radiation thermometer for measuring a temperature by infrared in a wavelength region that the carboxylic acid does not absorb, and the chamber comprises two transmissive windows corresponding to the first thermometer and the second thermometer.

Effect of the Invention

According to the embodiments of the present invention, the concentration of the carboxylic acid gas in the chamber can be estimated in non-contact and in real time. Further, since there is no need of collecting the carboxylic acid gas, contact with or inhalation of the highly irritating formic acid gas in particular can be avoided, and the concentration of the carboxylic acid gas can be very safely estimated. Still further, the amount of the carboxylic acid in the chamber can be obtained from the concentration of the carboxylic acid gas.

Therefore, in the acid treatment with the carboxylic acid gas, there are advantages such that the carboxylic acid gas concentration in the chamber can be controlled at a minimum concentration that allows a reduction reaction to progress; a cost can be saved due to suppressed introduction of excess carboxylic acid in the chamber; an end of the acid treatment can be determined by knowing a change in the carboxylic acid gas concentration in the chamber; and the like.

Further, after the acid treatment, when the carboxylic acid gas in the chamber is discharged, the completion of discharge can be determined. Therefore, a chamber material can be prevented from being corroded due to a long time exposure to the carboxylic acid gas.

DETAILED DESCRIPTION OF EMBODIMENTS

Figure 1:
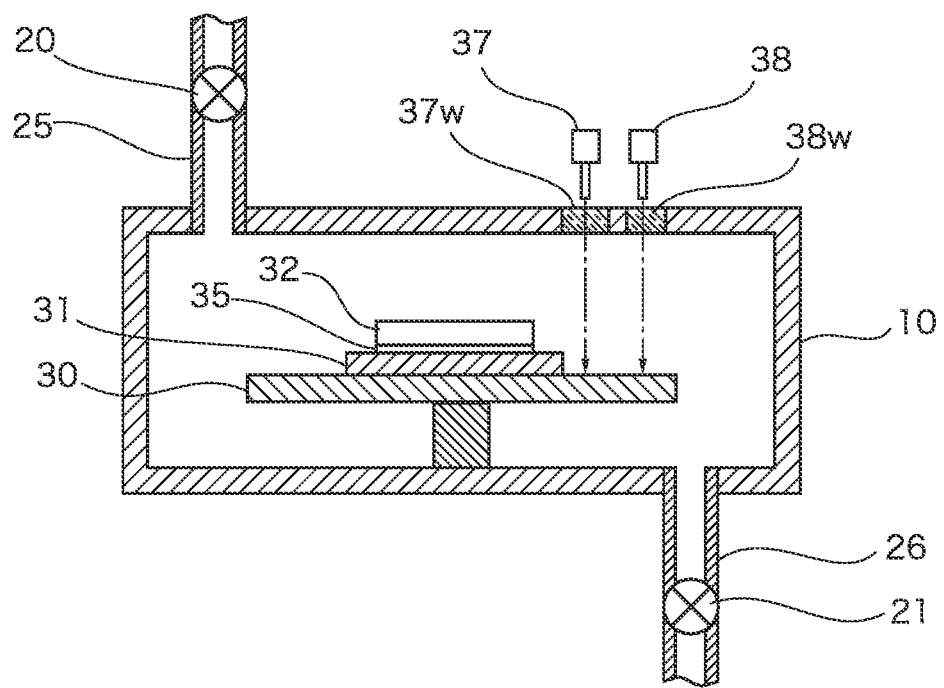
FIG. 1 is a schematic diagram, showing an embodiment of a soldering apparatus of an embodiment of the present invention.

Hereinafter, embodiments of the present invention will be described in more detail with reference to the drawings. FIG. 1 is a configuration diagram, showing a suitable embodiment of a soldering apparatus to which a method of estimating a concentration of a carboxylic acid gas according to the present invention is suitably applied. As the carboxylic acid in the embodiment of the present invention, formic acid, acetic acid, acrylic acid, propionic acid, caproic acid, oxalic acid, succinic acid, malonic acid, caprylic acid, caproic acid or the like can be used.

The method of estimating a concentration of carboxylic acid gas according to an embodiment of the present invention is a method of estimating the concentration of the carboxylic acid gas in a chamber into which carboxylic acid gas for reaction is introduced. Specifically, it is a method of estimating the concentration of the carboxylic acid gas for reaction in the chamber 10 in which an oxide deposited on a surface of members to be joined such as a substrate, a semiconductor chip, an electrode and the like that are placed on a heating stage 30 in the chamber and heated to a predetermined temperature is removed by a mixed gas of an inert gas and the carboxylic acid gas. As the inert gas, nitrogen, helium, argon and the like can be used. However, readily obtainable nitrogen is preferably used.

The chamber 10 is a vacuum chamber for removing an oxide film deposited on the surface of the members 31, 32 and for joining these members. The heating stage 30 is used to bear a pair of the members 31, 32 thereon that sandwich a solder 35 therebetween, then heat the members 31, 32 to a temperature equal to or higher than the reduction temperature of carboxylic acid and lower than the melting point of the solder to remove the oxide film, and after the end of the removal of the oxide film, heat to a temperature where the solder melts.

FIG. 1 shows a configuration example of the soldering apparatus, including: gas introduction means 25 for introducing the mixed gas of the inert gas and the carboxylic acid gas; the heating stage 30 for bearing the members 31, 32 thereon that sandwich the solder 35 therebetween and heating the members to a predetermined temperature; gas discharging means 26 for discharging gas; and the chamber 10 provided with a set of a first thermometer 37 and a transmissive window 37w and a set of a radiation thermometer 38 as a second thermometer and a transmissive window 38w.

As shown in FIG. 1, the gas introduction means 25 may be configured to introduce the mixed gas of the inert gas and carboxylic acid gas which have been mixed in advance into the chamber 10 through one line or may be configured to introduce each of the inert gas and the carboxylic acid gas into the chamber 10 in separate lines or may be configured to spray the carboxylic acid gas into the inert gas. Further, a method of preparing the mixed gas of the inert gas and the carboxylic gas is not particularly limited. For example, the mixed gas can be conditioned by vaporizing a predetermined amount of the carboxylic acid in the inert gas within a separate container connected with the gas introduction means 25. The carboxylic acid gas concentration in the mixed gas may be obtained from a ratio of amounts of introduced gasses, or may be obtained by measuring with the gas chromatograph or the FTIR.

Although the concentration of the carboxylic acid gas in the mixed gas to be introduced into the chamber 10 is not particularly limited, a concentration of 1.5% by volume or more is preferable in view of the reactivity. In this way, the oxide film deposited on a surface of the solder or the members to be joined can be readily removed, a solder wetting and spreading property becomes excellent, and generation of a void can be reduced in a soldering part. The carboxylic acid gas concentration of 1.5% by volume or more and 3% by volume or less is more preferable. The reason why the preferable concentration of carboxylic acid gas is 1.5% by volume or more is because this does not hinder the acid treatment by carboxylic acid, and the reason why it is 3% by volume or less is because a concern of corrosion of a chamber material by carboxylic acid can be reduced.

The gas discharging means 26 is connected to a vacuum pump (not shown) and is used to forcibly discharge gases from the inside of the chamber 10 to form a vacuum state before the inert gas and carboxylic acid gas are introduced and the acid treatment is started. By forcibly discharging gases from the inside of the chamber 10, an oxygen gas or the like that disturbs the acid treatment is removed. Under this vacuum condition, the carboxylic acid gas introduced into the chamber 10 can be readily vaporized and dispersed. The gas discharging means 26 is used to discharge a gas remaining in the chamber 10 after the acid treatment.

According to an embodiment of the present invention, a thermometer (first thermometer) for measuring a temperature without any influence of an infrared absorption by carboxylic acid and a radiation thermometer (second thermometer) for measuring a temperature by an infrared in a wavelength region that the carboxylic acid absorbs are used to measure a surface temperature of the same object in the chamber at the same point in time. Then, when the predetermined same object is measured at the same point in time, a temperature difference ($\Delta Tx$) is generated between the temperatures indicated by the first thermometer and the second thermometer. In this way, the concentration of the carboxylic acid gas in the chamber is estimated from a degree of the temperature difference ($\Delta Tx$).

That is, both of the first thermometer and the radiation thermometer as the second thermometer measure the surface temperature of the same object placed in the chamber. "To measure at the same point in time" "the surface temperature of the same object" means that the two thermometers simultaneously measure the temperature of the object having the same surface temperature. Further, "the object placed in the chamber" means an object placed in a room (chamber) where a carboxylic acid treatment is carried out. Therefore, the object placed in the chamber may be the members to be joined, an arbitrary object placed in the chamber, or an object placed for temperature measurement, without limiting to the heating plate such as the heating stage 30 or the like.

As the first thermometer 37, it is necessary to use a thermometer that is not influenced by the infrared absorption by the carboxylic acid gas. As such thermometer, a contact type thermometer, for example, a mercury thermometer, a resistance thermometer, a thermocouple thermometer or the like, or a non-contact type thermometer, for example, a radiation thermometer for measuring a temperature by infrared in a wavelength region that the carboxylic acid gas does not absorb or the like can be applied. The first thermometer also has a function of controlling a temperature of the heating stage 30 at a predetermined temperature.

Figure 2:
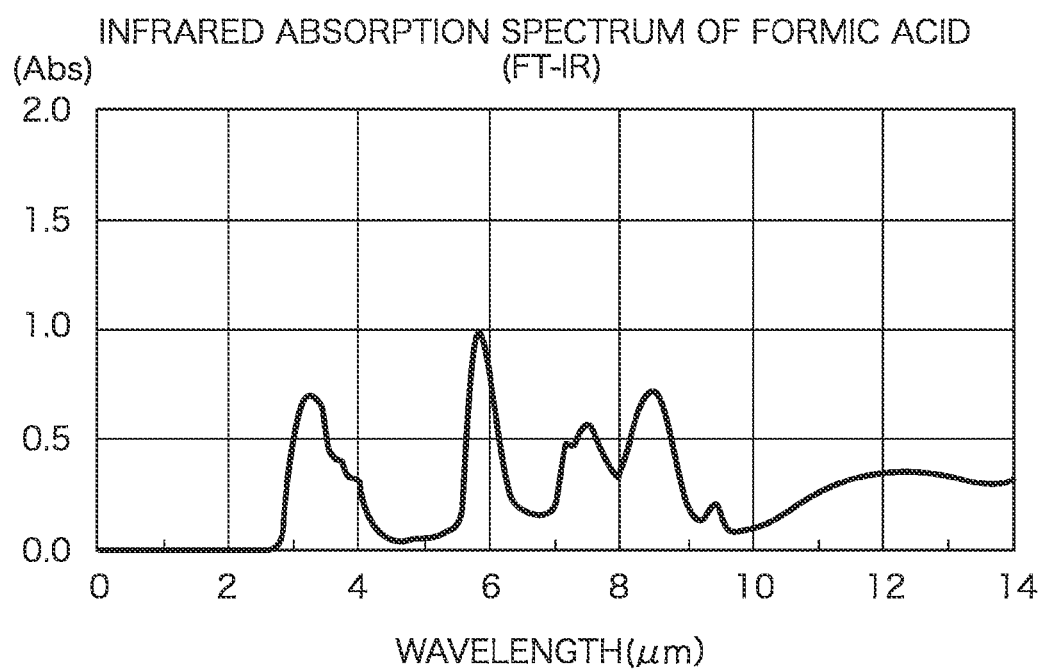
FIG. 2 is a graph, showing an infrared absorption spectrum of formic acid.

In the case where a radiation thermometer is used as a first thermometer, this radiation thermometer may be of a type used generally in a soldering apparatus as long as it can measure the temperature without being influenced by the carboxylic acid. For the formic acid, as shown in an infrared absorption spectrum in FIG. 2, wavelengths of the infrared that the formic acid absorbs are in regions of between 2.5 μm and 4.0 μm, between 5.5 μm and 6.0 μm, and between 7.0 μm and 14.0 μm. Therefore, for example, a radiation thermometer including InSb as a detecting element and a band-path filter for measuring the temperature by the infrared in the wavelength region between 4.5 μm and 5 μm that the formic acid does not absorb can be used.

On the other hand, as the radiation thermometer 38 that is the second thermometer (hereinafter, referred to as "the second radiation thermometer"), a radiation thermometer that can measure a temperature by the infrared in the wavelength region that the carboxylic acid gas absorbs is used. Therefore, the temperature of the heating stage 30 that is measured by the second radiation thermometer 38 is influenced by the carboxylic acid gas concentration in the chamber 10. Since a radiation thermometer with a detecting element for detecting the infrared in the above-described region that the carboxylic acid absorbs is used as the second radiation thermometer, a radiation thermometer having a thermopile as a detecting element that can measure a temperature by the infrared of wavelength between 8 μm and 13 μm, for example, can be used.

It should be noted that when the radiation thermometer is used as the first thermometer 37 and when the second radiation thermometer 38 is used, it is desirable that the temperature of the heating stage 30 is measured in a state where the carboxylic acid gas is not present and these thermometers are calibrated in advance such that these measured temperatures may coincide with a temperature measured by a contact type thermometer such as a thermocouple or the like.

Installation positions of the first thermometer 37 and the second radiation thermometer 38 are not particularly limited. However, in general, the contact type thermometer is frequently installed in the chamber 10. On the other hand, when the radiation thermometer is used as the first thermometer, these two radiation thermometers can also be installed in the chamber 10. When the radiation thermometer is installed in the chamber 10, there is a concern that a measurement error of the temperature becomes large because the radiation thermometer detects heat radiated from the radiation thermometer itself and also heat radiated from a floor or a wall of the chamber. Therefore, as shown in FIG. 1, two radiation thermometers are preferably installed outside of the chamber 10.

If the radiation thermometers are installed outside of the chamber 10, transmissive windows are disposed so that radiation heat (infrared) can transmit outside of the chamber 10. In order to prevent the infrared from entering the radiation thermometer from other than the heating stage 30 such as a floor, a wall or the like of the chamber 10, it is better to provide the transmissive windows having an area as small as possible and to dispose the transmissive windows corresponding to the radiation thermometers respectively. In FIG. 1, there is shown an example in which the transmissive window 37w corresponds to the first thermometer 37, and the transmissive window 38w corresponds to the second radiation thermometer 38.

The transmissive windows are preferably formed of a material that does not absorb the infrared, such as $BaF_2$, $CaF_2$ and ZnSe.

The acid treatment and the joining process performed by using the soldering apparatus according to the embodiment of the present invention are not particularly limited and may be a well-known process or the like. For example, a following process may be applied. First, on the heating stage 30 within the chamber 10, the members to be joined 31, 32 that sandwich the solder 35 therebetween are placed. A gas such as air present in the chamber 10 is forcibly discharged through the gas discharging means 26 by a vacuum pump. Simultaneously, the heating stage 30 is heated. The temperature of the heating stage 30 is measured in real time. After confirming that the temperature of the members 31, 32 has reached the predetermined temperature, a valve 21 is closed to disconnect the gas discharging means 26 and the chamber 10. Alternatively, after the inside of the chamber is depressurized by forcibly discharging the gas such as air present in the chamber 10 by the vacuum pump, the valve 21 is closed to disconnect the gas discharging means 26 and the chamber 10, and then the heating stage 30 may be heated. Thus, compared with the case where the heating is performed simultaneously with the forcible discharge of gas, the heating stage 30 can be heated to the predetermined temperature in a shorter time. Subsequently, a valve 20 is opened, the mixed gas of the inert gas and the carboxylic acid gas is introduced by the gas introducing means 25 for the mixed gas of the inert gas and the carboxylic acid gas, the inside of the chamber 10 is filled with the mixed gas of the inert gas and the carboxylic acid gas, and the acid treatment is performed.

That is, the method for estimating the concentration of the carboxylic acid gas according to the embodiment of claim 1, during the acid treatment, a surface temperature of the heating stage 30 is measured with two thermometers, one thermometer that is not influenced by the carboxylic acid and the other thermometer that is influenced by the carboxylic acid, thereby to estimate the concentration of the carboxylic acid gas in the chamber 10. The first thermometer 37 is a contact type thermometer such as a mercury thermometer, a resistance thermometer, a thermocouple thermometer or the like, or, as described above, a radiation thermometer that measures a temperature by infrared in a wavelength region that the carboxylic acid gas does not absorb, and the measured temperature is an actual temperature of the heating stage 30 because it is not influenced by the carboxylic acid gas. On the basis of the measured temperature of the first thermometer 37, the surface temperature of the heating stage 30 is controlled, and an acid treatment temperature is kept within a predetermined temperature range. The first thermometer 37 can be used to measure and maintain the surface temperature when heating the heating stage 30 to a melting temperature of the solder after the end of the acid treatment.

The second radiation thermometer 38 is, as described above, a radiation thermometer for measuring a temperature by infrared in the region that the carboxylic acid gas absorbs. The surface temperature of the heating stage 30 measured by the second radiation thermometer does not show an actual temperature of the heating stage 30 because it is influenced by the carboxylic acid gas. That is, the second radiation thermometer 38 shows a temperature lower than the actual temperature in accordance with an amount of the infrared absorbed by the carboxylic acid gas. Further, the amount of the infrared absorbed by the carboxylic acid gas is proportional to the concentration of the carboxylic acid gas. For example, under condition of constant temperature, the temperature indicated by the second radiation thermometer 38 becomes lower as the carboxylic acid gas concentration becomes higher, the temperature indicated by the second radiation thermometer 38 becomes higher as the carboxylic acid gas concentration becomes lower. When the second radiation thermometer 38 shows a temperature that is the same as the temperature indicated by the first thermometer 37, the concentration of the carboxylic acid gas is zero. Thus, whether the carboxylic acid gas concentration is high or low can be estimated from the temperature difference between the temperatures that the first thermometer and the second radiation thermometer indicate.

As the acid treatment progresses, the carboxylic acid gas concentration in the chamber 10 decreases and becomes substantially constant after the end of the acid treatment. Therefore, the temperature indicated by the second radiation thermometer 38 is low at the time of start of the acid treatment, rises gradually as the acid treatment progresses, and becomes substantially constant after the end of the acid treatment. Thus, a progress status of the acid treatment can be determined from the temperature indicated by the second radiation thermometer 38 in real time.

Now, it is known that intensity of infrared radiated from an object is influenced by a temperature thereof and increases as the temperature becomes higher. Therefore, when the carboxylic acid gas concentration during the acid treatment is measured by using the second radiation thermometer 38, it is an important requisite that the temperature in the chamber 10 is constant. However, in an embodiment of the present invention, there is no problem in this point because the temperature of the heating stage 30 is measured with the first thermometer 37 in real time and controlled so as to keep a predetermined temperature.

Further, in a method for estimating a concentration of a carboxylic acid gas according to the embodiment of claim 2, while changing the carboxylic acid gas concentration in a mixed gas of an inert gas and the carboxylic acid gas, the surface temperature of the heating stage 30 is measured with the first thermometer 37. While controlling the temperature of the heating stage 30 to a predetermined temperature on the basis of the measured temperature, the surface temperature of the heating stage 30 is measured with the second radiation thermometer 38. Then, by obtaining a temperature difference ($\Delta T$) between the temperatures indicated by the first thermometer 37 and the second radiation thermometer 38 and then by preparing in advance a calibration line that shows the relationship of the concentration of the carboxylic acid gas and the temperature difference ($\Delta T$) and using the calibration line, from a temperature difference ($\Delta Tx$) of the surface temperature of the heating stage 30 by the first thermometer and the second radiation thermometer, the concentration of the carboxylic acid gas in the chamber 10 can be determined.

That is, when the calibration line that shows the relationship between the carboxylic acid gas concentration and the temperature difference ($\Delta T$) is prepared in advance, only by obtaining the temperature difference $\Delta Tx$ in the chamber 10 in which carboxylic acid gas concentration is unknown, the carboxylic acid gas concentration can be quantitatively determined.

The calibration line of the formic acid can be prepared, for example, in the following manner. After evacuating the chamber 10, the heating stage 30 placed in the chamber is heated to a predetermined temperature. Then after the temperature of the heating stage 30 is stabilized, a mixed gas of a formic acid gas whose concentration is known and an inert gas is introduced into the chamber 10. A temperature ($T_1$) that the first thermometer 37 indicates and a temperature ($T_2$) that the second radiation thermometer 38 indicates are simultaneously measured, and a temperature difference ($\Delta T$) between $T_1$ and $T_2$ is determined. With changing the formic acid gas concentration, a similar operation is repeated. Further, with changing the temperature of the heating stage 30, a similar operation is repeated. At the end, for every temperature of the heating stage 30, the relationship between the formic acid gas concentration (%) and the temperature difference ($\Delta T$) is plotted and approximating by a linear regression line, the calibration line is sufficient.

The carboxylic acid gas concentration for preparing the calibration line can be optionally set. For example, in the case of removing an oxide film by the formic acid, a preferable range of the formic acid gas used is 1.5 to 3% by volume. When considering that the formic acid gas concentration decreases by the acid treatment, the calibration line of the concentration up to about 3% by volume may be prepared.

As described above, the intensity of the radiated infrared changes depending on the temperature of the heating stage 30 because the intensity of the radiated infrared is different depending on the temperature of the object. Therefore, even when an amount of the infrared that the carboxylic acid gas absorbs is the same, the temperature indicated by the second radiation thermometer 38 is different for different acid treatment temperatures. Therefore, the calibration line has to be prepared for every acid treatment temperature because the relationship between the carboxylic acid gas concentration and the temperature difference ($\Delta T$) varies depending on the temperature.

When the calibration line is prepared, by optionally setting a temperature range and by preparing a plurality of the calibration lines corresponding to each of acid treatment temperatures in advance, the carboxylic acid gas concentration can be known for a wide range of temperature. By preparing the calibration lines that show the relationship between the carboxylic acid gas concentration and the temperature difference ($\Delta T$) under a plurality of conditions different in the acid treatment temperature and by obtaining a relational expression that shows the relationship between a gradient of the calibration line and the acid treatment temperature, a gradient of the calibration line at a predetermined acid treatment temperature can be determined from the relational expression. Then, by determining the carboxylic acid gas concentration in the chamber from the gradient of the calibration line and the temperature difference ($\Delta Tx$), the carboxylic acid gas concentration can be estimated. From a viewpoint such that there is a case where, in the chamber of normal temperature under evacuation, the mixed gas of the inert gas and the carboxylic acid gas is introduced in advance, or almost all solder is molten at 350° C., or the like, when the calibration lines are prepared in the range of from normal temperature to 350° C., the carboxylic acid gas concentrations in the soldering treatment and the soldering apparatus can be estimated.

Further, a width of the temperature for which the calibration line is prepared is not particularly limited but may be appropriately selected in the range between 25° C. and 50° C. in accordance with measurement precision of the carboxylic acid concentration. For example, when the acid treatment temperature is set to 150° C., by preparing the calibration lines at an interval of 50° C. between 100° C. and 300° C., the formic acid concentration can be estimated with high precision in the range between 100° C. and 300° C.

An amount of the carboxylic acid in the chamber can be also estimated by using the carboxylic acid gas concentration estimated by the method for estimating the carboxylic acid gas concentration according to the embodiment of the present invention. Specifically, after determining the amount of the carboxylic acid gas in the chamber by multiplying a chamber volume by the carboxylic acid gas concentration, and by converting a pressure in the chamber into normal pressure, the amount of the carboxylic acid gas in the chamber can be determined. It should be noted that the pressure in the chamber is a pressure in the chamber at a point of time of a measurement of a temperature difference ($\Delta Tx$) between the temperatures indicated by the first thermometer and the second thermometer.

EXAMPLES

Hereinafter, the present invention will be described in more detail with reference to some examples. However, the present invention is not limited to the following examples.

Example 1

In a configuration shown in FIG. 1, a test was performed using a soldering apparatus provided with a chamber 10 having a capacity of 20 liters. After evacuating the chamber 10, a heating plate (heating stage 30) disposed in the chamber was heated to 150° C. and after stabilization of the temperature, a mixed gas of a formic acid gas having a concentration of 2.4% and an inert gas was introduced into the chamber. A temperature ($T_1$) indicated by the first thermometer 37 and a temperature ($T_2$) indicated by the second radiation thermometer 38 were simultaneously read, and a temperature difference of $T_1$ and $T_2$ ($\Delta T$) was determined. Then the similar operation was repeated with change of the formic acid gas concentration to 1.2% and 0.6%. See FIG. 3.

The similar operation was repeated with change of the temperature of the heating plate to 250° C. and 350° C. See FIG. 4.

For every temperature of the heating plate, the relationship between the formic acid gas concentration (%) and the temperature difference ($\Delta T$) was plotted and approximated with a linear regression line to prepare a calibration line. See FIG. 5.

Figure 5:
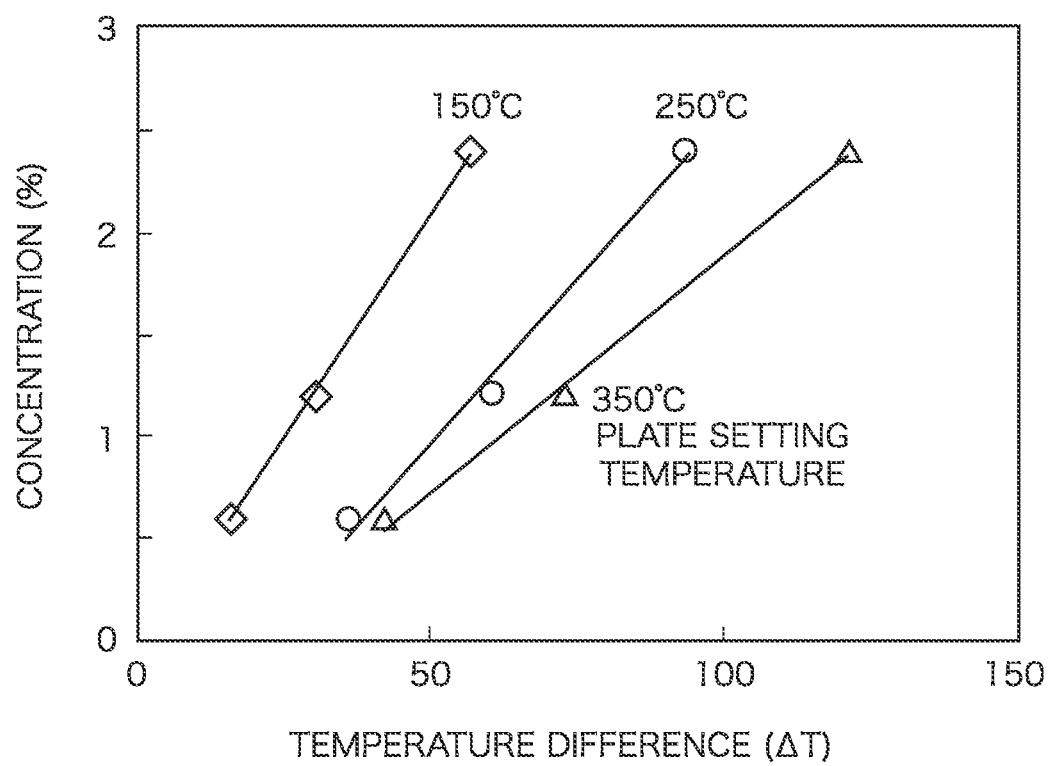
FIG. 5 depicts calibration lines, showing a relationship of a carboxylic acid gas concentration (%) and a temperature difference (ΔT).

Further, regarding three calibration lines in FIG. 5, with the acid treatment temperature (plate setting temperature) in a horizontal axis and with a gradient (%/$\Delta T$) of the calibration line in a vertical axis, a relational expression (linear regression line) showing the relationship between the gradient of the calibration line and the acid treatment temperature was prepared. See FIG. 6.

Figure 3:
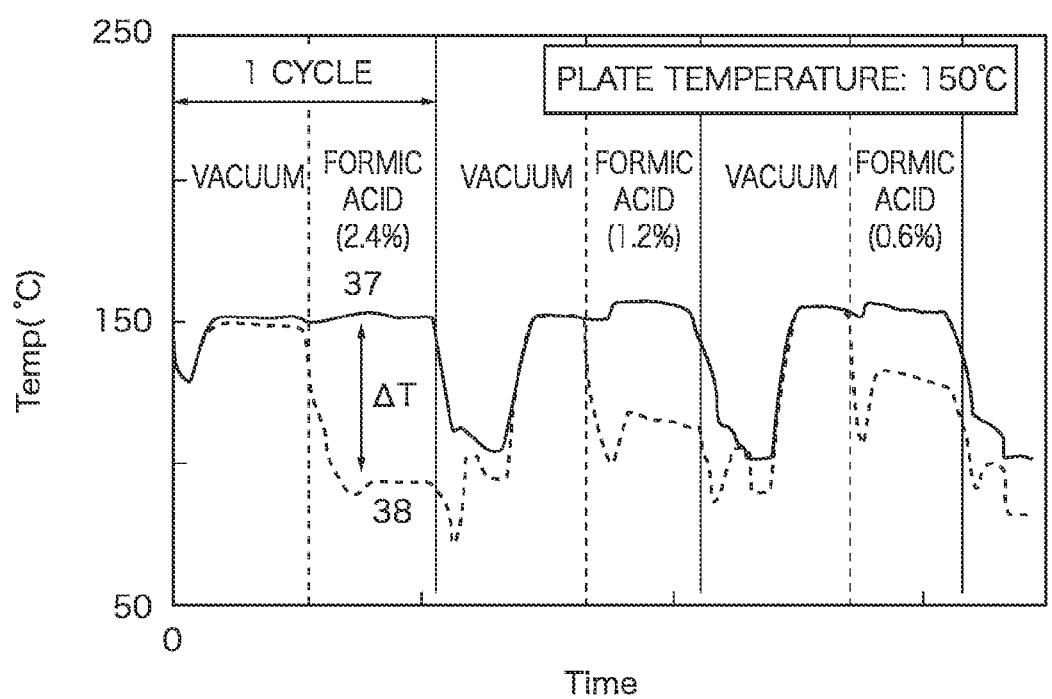
FIG. 3 is a graph, showing temperatures measured by a first thermometer and a second thermometer for each of formic acid concentrations.
Figure 4:
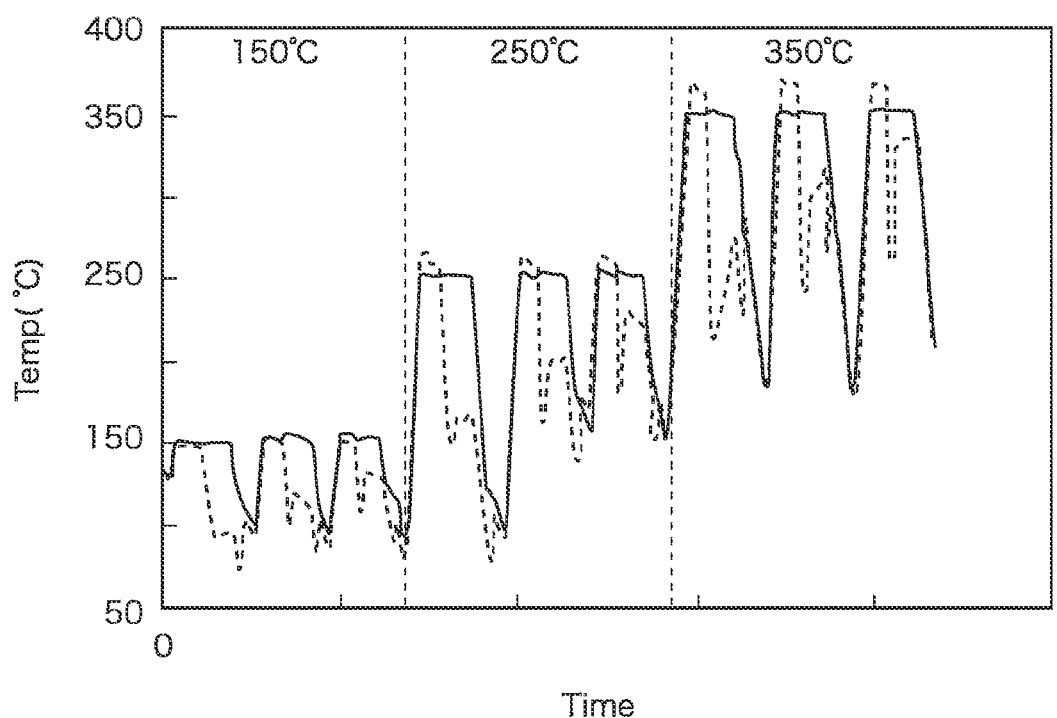
FIG. 4 is a graph, showing temperatures measured by the first thermometer and the second thermometer for each of measured temperatures.

FIG. 3 and FIG. 4 shows that the higher the formic acid gas concentration is, the larger the temperature difference ($\Delta T$) becomes. In the case where the formic acid gas concentrations are the same, the higher the temperature of the heating plate is, the larger the temperature difference ($\Delta T$) becomes. Thus, by measuring the temperature difference ($\Delta T$), the formic acid gas concentration in the chamber can be estimated. Further, by using the calibration line of FIG. 5, the formic acid gas concentration can be quantitatively determined.

Example 2

Figure 6:
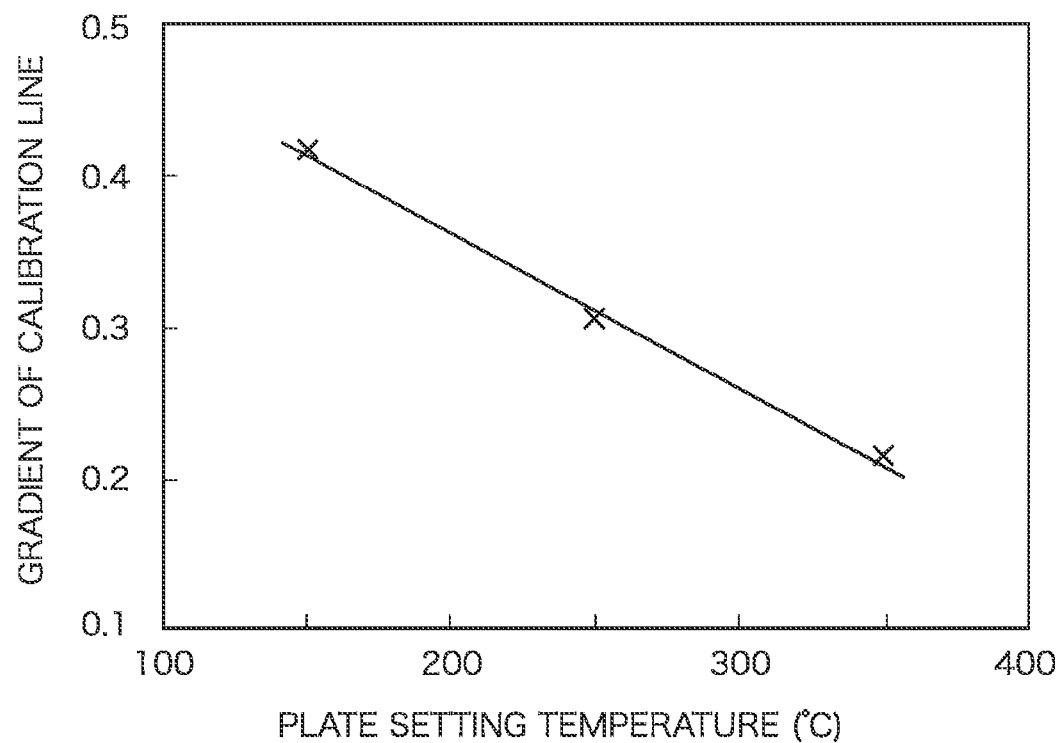
FIG. 6 is a graph, showing a relationship of an acid treatment temperature and a gradient of the calibration line.

The gradient of the calibration line at the acid treatment temperature of 200° C. can be determined as 0.37 (%/$\Delta T$) using the linear regression line prepared in Example 1 (FIG. 6). Further, from the gradient of the calibration line and measured temperature difference ($\Delta T$) of two thermometers at the acid treatment temperature of 200° C., the carboxylic acid gas concentration in the chamber can be calculated.

Example 3

An amount of the carboxylic acid at the acid treatment temperature of 200° C. can be calculated by multiplying the carboxylic acid gas concentration calculated in Example 2 by the chamber capacity (20 liters) to calculate an amount of the carboxylic acid gas in the chamber, and by converting this amount from a pressure in the chamber at the time of temperature measurement to a normal pressure.

INDUSTRIAL APPLICABILITY

As described above, the method for estimating concentration of the carboxylic acid gas of the present invention is useful for a) knowing the concentration of the carboxylic acid gas in the chamber after the end of the acid treatment process, b) knowing the change of the concentration of the carboxylic acid gas in the case where the temperature is changed during the acid treatment process, and c) tracking the variation in the concentration of the carboxylic acid gas in the soldering apparatus. Further, the soldering apparatus for estimating the carboxylic acid gas concentration in the chamber is also useful for improvement of the productivity due to shortening of the soldering process.

EXPLANATION OF REFERENCE NUMERALS 10 chamber
20 valve
21 valve
25 gas introduction means
26 gas discharging means
30 heating stage
31 member
32 member
35 solder
37 first thermometer
37W transmissive window
38 second radiation thermometer
38W transmissive window

The invention claimed is:

1. A method for manufacturing a bonded member, comprising the steps of:
   estimating a concentration of a carboxylic acid gas in a chamber, the carboxylic acid gas introduced into the chamber being for reaction;
   wherein the step of estimating the concentration of the carboxylic acid includes the steps of:
   measuring a surface temperature of a same object placed in the chamber at a same point in time by using a thermometer (first thermometer) for measuring a temperature without any influence of infrared absorption by carboxylic acid, and a radiation thermometer (second thermometer) for measuring a temperature by infrared in a wavelength region that the carboxylic acid absorbs; and
   estimating the concentration of the carboxylic acid gas in the chamber on the basis of a temperature difference ($\Delta Tx$) between temperatures indicated by the first thermometer and the second thermometer,
   the method further comprising,
   controlling the carboxylic acid gas concentration in the chamber based on the estimated concentration of the carboxylic acid gas,
   placing members to be joined, the members sandwiching a solder, on a heating stage within the chamber;
   heating the heating stage to a temperature equal to or higher than a reduction temperature of carboxylic acid and lower than a melting temperature of the solder;
   performing acid treatment to the solder; and
   heating the heating stage to the melting temperature of the solder after an end of the acid treatment.

2. The method for manufacturing a bonded member according to claim 1,
   wherein the first thermometer is a radiation thermometer for measuring a temperature by the infrared in a wavelength region that the carboxylic acid does not absorb.

3. A method for manufacturing a bonded member, the method comprising the steps of:
   estimating a concentration of a carboxylic acid gas in a chamber, the carboxylic acid gas introduced into the chamber being for reaction;
   wherein the step of estimating the concentration of the carboxylic acid includes the steps of:
   measuring, while changing a concentration of the carboxylic acid gas for reaction, a surface temperature of a same object placed in the chamber at a same point in time by using a thermometer (first thermometer) for measuring a temperature without any influence of infrared absorption by carboxylic acid, and a radiation thermometer (second thermometer) for measuring a temperature by infrared in a wavelength region that the carboxylic acid absorbs;
   preparing in advance a calibration line showing a relationship of the carboxylic acid gas concentration and a temperature difference ($\Delta T$) by obtaining the temperature difference (ΔT) between temperatures indicated by the first thermometer and the second thermometer; and estimating the concentration of the carboxylic acid gas in the chamber on the basis of the prepared calibration line and the temperature difference (ΔTx) between temperatures indicated by the first thermometer and the second thermometer for a surface temperature of the same object placed in the chamber, the method further comprising, placing members to be joined, the members sandwiching a solder, on a heating stage within the chamber;

heating the heating stage to a temperature equal to or higher than a reduction temperature of carboxylic acid and lower than a melting temperature of the solder;

performing acid treatment to the solder; and heating the heating stage to the melting temperature of the solder after an end of the acid treatment.

4. The method for manufacturing a bonded member according to claim 3, wherein the step of estimating the concentration of the carboxylic acid gas according to claim 3, further including the steps of:

preparing the calibration lines showing a relationship of the carboxylic acid gas concentration and the temperature difference (ΔT) under a plurality of conditions different in an acid treatment temperature;

obtaining a relational expression showing a relationship of a gradient of the calibration line and the acid treatment temperature, obtaining a gradient of the calibration line in a predetermined acid treatment temperature from the relational expression, and estimating the concentration of carboxylic acid gas in the chamber on the basis of the gradient of the calibration line and the temperature difference (ΔTx).

5. The method for manufacturing a bonded member according to claim 3, wherein the first thermometer is a radiation thermometer for measuring a temperature by the infrared in a wavelength region that the carboxylic acid does not absorb.

6. A method for manufacturing a bonded member, the method comprising the steps of:

providing a soldering apparatus capable of estimating a concentration of a carboxylic acid gas in a chamber, the soldering apparatus including, a heating stage;

a gas introducing part for introducing a mixed gas of an inert gas and a carboxylic acid gas; and a chamber having a gas discharging part;

wherein the chamber comprises a thermometer (first thermometer) for measuring a temperature without any influence of infrared absorption by carboxylic acid, and a radiation thermometer (second thermometer) for measuring a temperature by infrared in a wavelength region that the carboxylic acid absorbs, the method further comprising the steps of:

estimating the concentration of the carboxylic acid gas in the chamber on the basis of a temperature difference (ΔTx) between temperatures indicated by the first thermometer and the second thermometer, controlling the carboxylic acid gas concentration in the chamber based on the estimated concentration of the carboxylic acid gas, placing members to be joined, the members sandwiching a solder, on a heating stage of the soldering apparatus;

heating the heating stage to a temperature equal to or higher than a reduction temperature of carboxylic acid and lower than a melting temperature of the solder;

introducing the carboxylic acid gas into an inside of the chamber;

performing acid treatment to the solder; and heating the heating stage to the melting temperature of the solder for manufacturing the bonded member after an end of the acid treatment.

7. The method for manufacturing a bonded member according to claim 6, wherein the first thermometer is a radiation thermometer for measuring a temperature by infrared in a wavelength region that the carboxylic acid does not absorb, and the chamber comprises two transmissive windows corresponding to the first thermometer and the second thermometer.

* * * * *